Figure 1A:
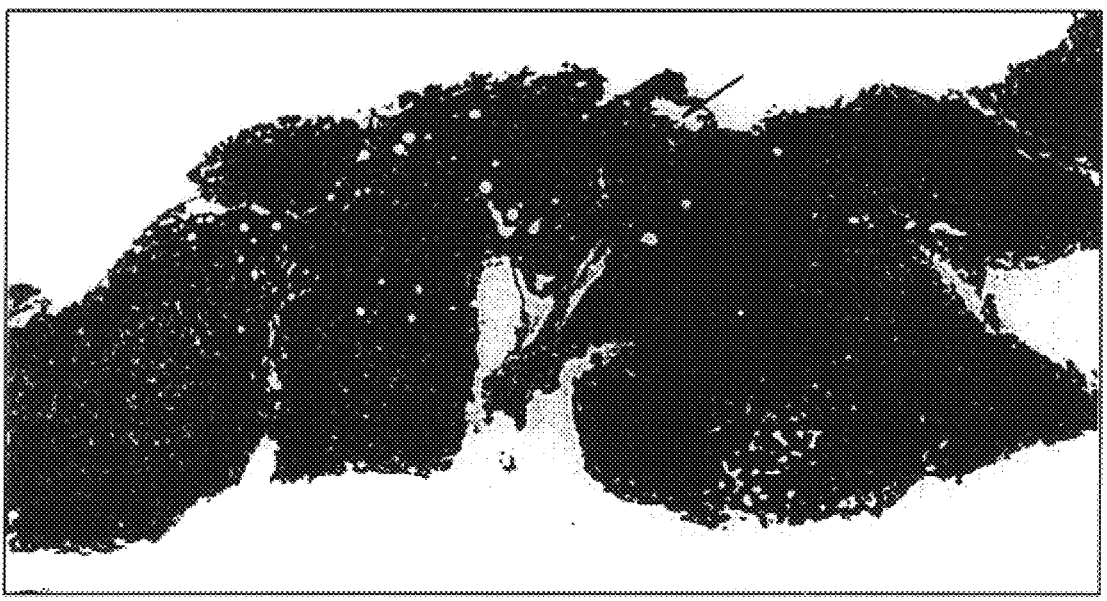

United States Patent [19]

Vierling

[11] Patent Number: 6,034,297
[45] Date of Patent: Mar. 7, 2000

[54] IN VIVO, ANIMAL MODEL FOR EXPRESSION OF HEPATITIS C VIRUS

[75] Inventor: John M. Vierling, Beverly Hills, Calif.

[73] Assignee: Cedars-Sinai Medical Center, Los Angeles, Calif.

[21] Appl. No.: 08/938,987

[22] Filed: Sep. 26, 1997

[51] Int. Cl.[7] .......................... A01K 67/00; A61K 48/00; C12N 15/00
[52] U.S. Cl. .................. 800/9; 800/21; 424/9.2; 424/93.1
[58] Field of Search ..................... 424/93.1, 9.2; 800/9, 21

[56] References Cited

U.S. PATENT DOCUMENTS

| | | | |
|---|---|---|---|
| 5,434,341 | 7/1995 | Outzen | 800/2 |
| 5,476,996 | 12/1995 | Wilson et al. | 800/2 |
| 5,476,997 | 12/1995 | Kaneshima et al. | 800/2 |
| 5,858,328 | 1/1999 | Reisner | 424/9.2 |

FOREIGN PATENT DOCUMENTS

| | | |
|---|---|---|
| WO 93/23084 | 11/1993 | WIPO. |
| WO 94/02601 | 2/1994 | WIPO. |
| WO 94/27556 | 12/1994 | WIPO. |
| WO 96/39810 | 12/1996 | WIPO. |

OTHER PUBLICATIONS

Proc. Natl. Acad. Sci. USA, vol. 92 pp. 4942–4946, May 1995 Medical Sciences Complete Reconstitution of Mouse Liver With Zenogeneic Hepatocytes Jonathan A. Rhim, Eric P. Sandgren, Richard D. Palmiter, Ralph L. Brinster.

The Journal of Infectious Diseases (1995), Hepatitis C Virus Viremia in SCID–BNX Mouse Chimera, pp. 25–30.

Jaffee, Bruce D., and Henry N. Claman, "Chronic Graft–versus–Host Disease (GVHD) as a Model for Scleroderma", Cellular Immunology, vol. 77, pp. 1–12 (1983).

Lerat, Hervé et al., "Specific Detection of Hepatitis C Virus Minus Strand RNA in Hematopoietic Cells," J. Clin Invest., vol. 97, No. 3, pp. 845–851, Feb. 1996.

Vierling, John M. et al., "Hepatic Lesions in Murine Chronic Graft–Versus–Host Disease to Minor Histocompatibility Antigens, A Reproducible Model of Non–suppurative Destructive Cholangitis," Transplantation, vol. 48, No. 4, pp. 717–718, Oct. 1989.

Veirling et al. Xenografting of Human HCV–Infected Liver into Sever Combined Immunodeficiency (SCID) Mice. Hepatology, vol. 24, No. 4, Pt. 2, p. 218A, Oct. 1996.

Medical Virology, Fourth Edition, White et al., eds. Academic Press, pp. 447–448, 1994.

Stedman's Medical Dictionary, 26th edition, Spraycar, ed. Williams & Wilkins, p. 1300, 1995.

*Primary Examiner*—Bruce R. Campell
*Assistant Examiner*—Deborah J. R. Clark
*Attorney, Agent, or Firm*—Pretty, Schroeder & Poplawski

[57] ABSTRACT

Disclosed is a method for expressing hepatitis C virus in an in vivo, animal model. Viable, hepatitis C virus-infected, human hepatocytes are transplanted into a liver parenchyma of a scid/scid mouse host. The scid/scid mouse host is then maintained in a viable state, for up to five days or greater, whereby viable, morphologically intact human hepatocytes persist in the donor tissue and hepatitis C virus is replicated in the persisting human hepatocytes.

31 Claims, 3 Drawing Sheets

FIG. 3A
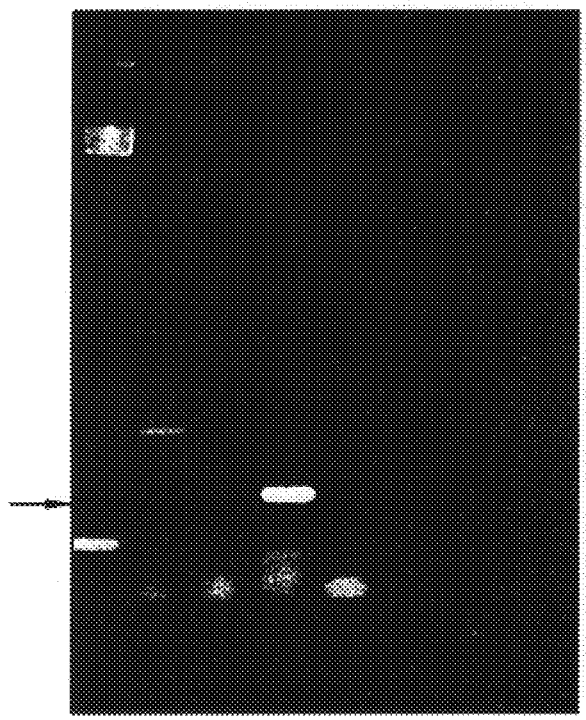
FIG. 3B
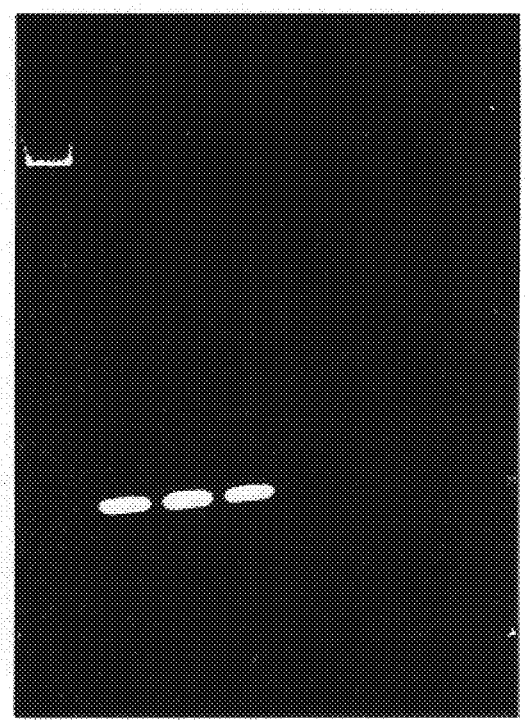
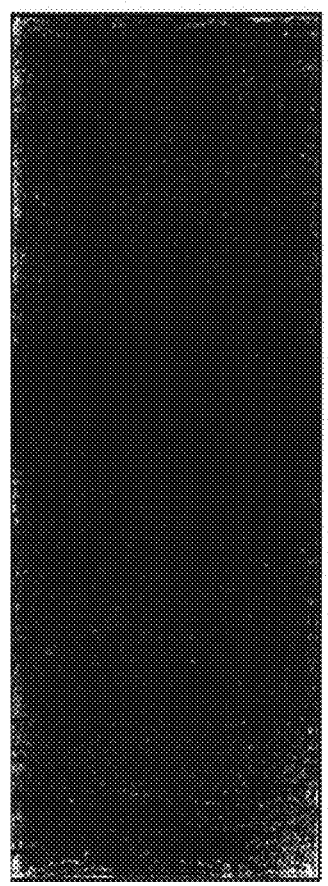
FIG. 3C

IN VIVO, ANIMAL MODEL FOR EXPRESSION OF HEPATITIS C VIRUS

BACKGROUND OF THE INVENTION

1. Field of the Invention

This invention relates to the medical arts. In particular, it relates to a model for studying hepatitis C virus and for a method for preparing the model.

2. Discussion of the Related Art

The use of heterologous transplants in a host has found wide application in research and therapy. The ability to transplant tissue from one host to another allows for opportunities of scientific investigation which are not available in the source host. For example, it has proved possible to create chimeras from severe combined immunodeficiency ("scid/scid" or "SCID") mice host and human donors for studies of the organ-specificity of metastatic malignance and functions of human leukocytes. However, no validated animal models for the expression of hepatitis C virus ("HCV") have been reported.

There has also been reported the grafting of xenogeneic tissue beneath the renal capsule of immunocompromised mouse hosts. However, the renal capsule as a site for introduction of xenogeneic tissue has many drawbacks. It is physically difficult to introduce the tissue, so that there is a significant number of failures in producing functional organs. Also, vascularization is not as extensive as one would wish. In addition, the tissue did not maintain a desirable growth pattern. There remains, therefore, interest in being able to develop alternative sites and methods for introduction of xenogeneic tissue into anatomical sites of target hosts.

In particular, there remains a definite need for an in vivo animal model for studying HCV. There remains a further definite need for a method for transplanting leukocyte depleted or relatively large HCV-infected liver tissue samples into the homologous organ. There remains a still further definite need for a method for transplanting xenogeneic HCV-infected hepatocytes that remain viable and morphologically intact in the donor tissue and replicate HCV. The present invention satisfies these and other needs and provides further related advantages.

SUMMARY OF THE INVENTION

The present invention, which addresses the above needs, is embodied in a method for expressing hepatitis C virus in an in vivo, animal model. Viable, hepatitis C virus-infected, human hepatocytes are transplanted into a liver parenchyma of a scid/scid mouse host. The scid/scid mouse host is then maintained in a viable state, for up to five days or greater, whereby viable, morphologically intact human hepatocytes persist in the donor tissue and hepatitis C virus is replicated in the persisting human hepatocytes.

In some embodiments, the scid/scid mouse host is an $H\text{-}2^d$ scid/scid mouse host. Further, in some embodiments the hepatocytes to be transplanted are obtained from a percutaneous liver biopsy and, in some embodiments, the hepatocytes are deleted of leukocytes prior to transplanting. The resulting human hepatic-SCID chimera provides and environment suitable for the persistence and function of the transplanted tissue and maintenance of the architectural arrangement of the human hepatocytes.

BRIEF DESCRIPTION OF THE FIGURES

FIGS. 1A and 1B show a percutaneous liver biopsy specimen from a patient with chronic hepatitis, under low and high power magnification, respectively.

FIGS. 2A–2C show a hepatitis C virus-infected, human liver tissue xenograft five days after transplantation in accordance with the invention, under three powers of magnification.

FIGS. 3A–3C show results of molecular virologic tests demonstrating the presence of hepatitis C viremia in the blood of the human hepatic-SCID chimera prepared in accordance with the invention.

DETAILED DESCRIPTION OF THE PREFERRED EMBODIMENT

Methods and chimeric immunocompromised heterologous mammalian hosts, particularly mouse hosts, are provided for the expression of hepatitis C virus ("HCV"). The chimeric hosts have transplanted in their liver parenchyma viable, hepatitis C virus-infected human liver tissue having morphologically intact hepatocytes. transplanted into a a viable, hepatitis C virus-infected human hepatocytes in the liver of an immunocompromised host.

The mammals are immunocompromised in normally inheriting the desired immune incapacity or the desired immune incapacity may be created. For example, host with severe combined immunodeficiency, known as scid/scid hosts, are available. Rodentia, particularly mice, and equine, particularly horses, are presently available as scid/scid hosts (hereinafter referred to as scid/scid hosts). The scid/scid hosts lack functioning lymphocyte types, particularly B-cells and some T-cell types. In the scid/scid mouse hosts, the genetic defect appears to be a non-functioning recombinase, for the germline DNA is not rearranged to produce functioning surface immunoglobulin and T-cell receptors.

The xenograft will occur with a host at an age less than about 25% of its normal lifespan, usually to 20% of the normal lifespan with mice, and the age will generally be of an age of abut 3 to 10 weeks, more usually from about 4 to 8 weeks. The mice may be of either sex, may be neutered, and may be otherwise normal, except for the immunocompromised state, or may have one or more mutations, which may be naturally occurring or as a result of mutagenesis.

The viable, human hepatocytes to be xenografted are obtained from human donors infected with HCV. It is an advantage of the invention that different HCV genotypes and HLA haplotypes can be studied by choosing tissue from different donors. The tissue may be fresh tissue, suitably obtained using a percutaneous liver biopsy, or freshly frozen tissue, tissue frozen within about 12 hours of such a biopsy and then maintained at below −10° C., usually at about liquid nitrogen temperature (−70° C.) indefinitely.

The hepatocytes may be provided as individual cells freed of attached stromal elements or as small tissue slices. To facilitate xenografting of HCV-infected hepatocytes for studies of human hepatic/viral gene expression in the absence of inflammation and to study the consequences of subsequent adoptive transfer of autologous effector cells, in some embodiments, it is desirable to first deplete the liver biopsy specimens of inflammatory cells. The specimens are rocked in a medium supplemented with DNAase I, collagenase D and hyaluronidase to disrupt the cell adhesion and gently pipetted to produce a single cell suspension containing hepatic parenchyma cells, biliary epithelial cells and mononuclear inflammatory cells. The cell suspension is then incubated with mAb specific for CD45 (mouse IgG1, K; PharMigen), that reacts with an antigen ubiquitously present on the surface membranes of human leukocytes. CD45+ is absent from non-hemopoetic cells, including all epithelial cells. Depletion of CD45+ cells is performed using immunomagenetic beads coated with anti-mouse Ig. The remaining hepatic cells are centrifuged into a pellet and mixed with a fresh drop of autologous blood (tail vein) to create a transplantable graft.

In other embodiments small tissue slices are transplanted. The small tissue slices are usually of length from about 0.5 mm to 4 mm, more usually from about 1 mm to 2 mm, and usually of a thickness in the range of about 1 to 2 mm, so that the sections can easily fit into a trocar used for implantation, usually conveniently of about 15- to 20 gauge. It is an advantage of the invention that such relatively large specimens can be used, because their large size facilitates both transplanting and the subsequent vascularization.

Methods of inserting the hepatocytes into the liver parenchyma of the mouse host are within the skill of the ordinary artisan. In a representative method, six to eight week-old, female, H-$2^d$ scid/scid mice are used as the hosts. Xenografting is performed through a 2 cm laparotomy incision created under methoxyfluorane general anesthesia The hepatocytes are transplanted into the parenchyma of the right hepatic lobe. Homeostasis is achieved with gelfoam, and the wound is closed with absorbable subcuticular sutures.

EXAMPLE

Liver biopsy

A percutaneous liver biopsy performed in a thirty-seven year-old adult woman was placed in Wisconsin preservation solution on ice and transported to a laboratory. At the laboratory, the biopsy specimen was extensively washed with Hank's balanced salt solution at room temperature to remove the preservation solution and the blood within the liver tissue's sinusoids.

Xenografting of Human Liver

The HCV-infected liver tissue was then transplanted into the liver of a six week-old female H-$2^d$ SCID mouse (obtained from Jackson Laboratory, Bar Harbor, Me.) anesthetized using inhaled methoxflurane in a Bell jar. Anesthesia was maintained during surgery using a nose cone. The abdominal hair was clipped and the abdomen skin was sterilized. A sterile plastic drape was placed over the abdomen, and a midline laparotomy was performed to expose the liver. Using a scalpel, a 3 mm incision was made parallel to the vascular planes of an hepatic lobe, and the wound was immediately packed with a gelfoam pledget soaked in sterile normal saline to create a pouch. Homeostasis was rapidly achieved and total blood loss was insignificant. After achieving homeostasis, the gelfoam pledget was removed, and the human liver biopsy segment was inserted into the pouch. The surface of the mouse liver spontaneously closed over the xenograft. The peritoneum and skin were closed with absorbable suture materials. The mouse regained consciousness in a few minutes and moved about normally.

Histopathology of the Hepatic Xenograft

Five full days after xenotransplantation, the mouse was euthanized using cervical dislocation under ketamine anesthesia. The liver containing the xenograft was excised and fixed in 10% buffered formalin for histopathological examination. Histologic sections were stained with hematoxylin and eosin.

Molecular Virologic Studies

Blood obtained at the time of euthanasia was centrifuged to prepare serum. RNA was extracted from both the mouse serum and the serum of a patient with documented hepatitis C viremia. HCV RNA PCR assays were performed using the one-step method described in Hu K-Q, Yu C-H and Vierling, "One Step RNA PCR for Detection of HCV RNA," *Heptology,* 1993; 18: 270–74, which reference is herein incorporated by reference. The HCV specificity of the cDNA products was confirmed using Southern blot hybridization with a $^{32}$P-labeled probe specific for HCV cDNA.

Histopathology of Liver Biopsy Specimen

Figure 1B:

FIGS. 1A and 1B show a percutaneous liver biopsy specimen from a patient with chronic hepatitis under low and high power magnification, respectively. At both low and high power magnification, micro- and macrovesicular fat can be seen in some hepatocytes.

Histopathology of Hepatic Xenograft

Figure 2A:
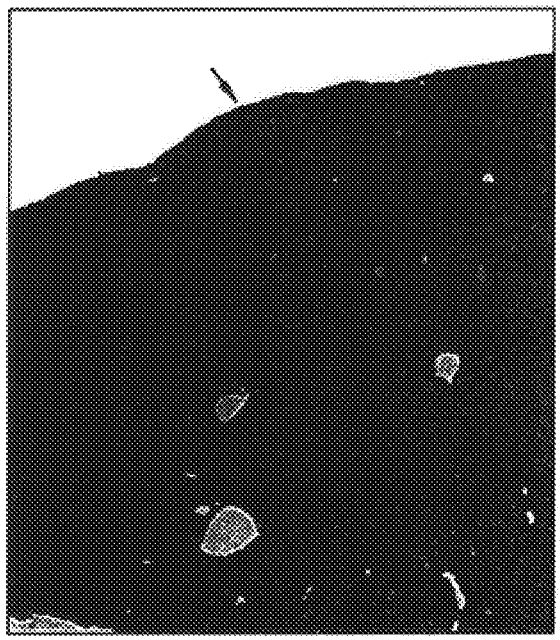
Figure 2B:
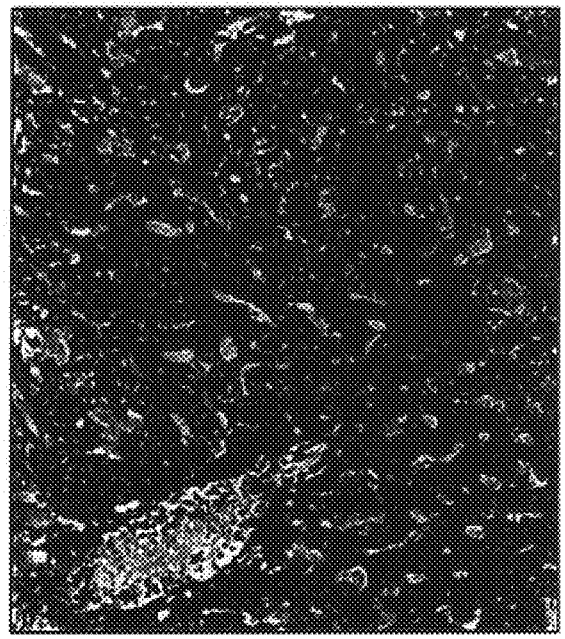
Figure 2C:
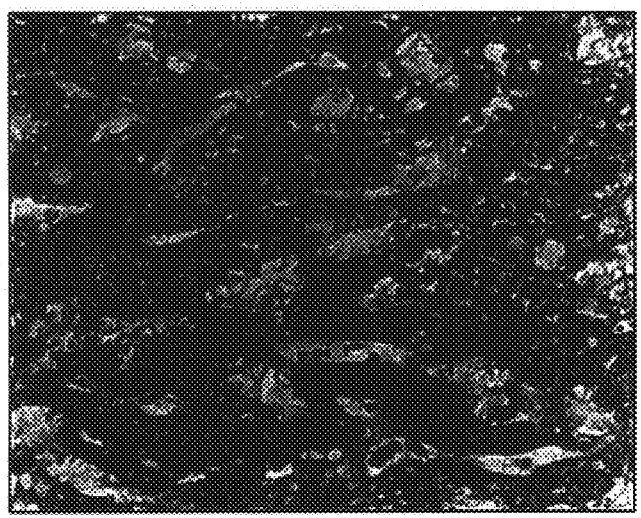

As seen in FIG. 2A, the human hepatic xenograft was readily distinguished from the adjacent mouse liver based on differences in hematoxylin and eosin staining characteristics. The normal architecture of the human parchenchyma was preserved with hepatocytes arranged in cords within sinusoids (FIG. 2B). The human hepatocytes continued to express both micro- and macrovesicular fat observed in the original biopsy (FIG. 2C).

HCV RNA PCR of Mouse Host Blood

The HCV RNA PCR results using mouse blood are shown in FIG. 3. Using the one-step HCV RNA PCR method (FIG. 3A), the appropriate size of cDNA product was observed using RNA isolated from the blood of the host mouse and the serum of a patient with documented HCV viremia. No reaction product was observed in the negative control (RNA isolated from the blood of a native scid/scid mouse). Using a "nested" HCV RNA PCR technique (FIG. 3B), the appropriate size of cDNA products were also observed for the host mouse and a positive control. No reaction product was observed in the negative control. Southern blot hybridization (FIG. 3C) confirmed the HCV-specificity of the cDNA products.

The inventive in vivo model permits study of HCV and host gene expression, in the presence and absence of host leukocytes, using infected liver tissue from human donors with different HCV genotypes and different HLA haplotypes. After maintaining the mouse for up to about five days or longer, the liver tissue is at least partially vascularized and generally highly vascularized. The liver tissue is not rejected, because of the severe immunodeficiency of the SCID mouse. Further, because the infected liver tissue is transplanted into a homologous organ, there is provided an environment suitable for the persistence and function of the grafted tissue and maintenance of the architectural arrangement of the human hepatocytes. The liver tissue grows rapidly, and assumes an architecture substantially similar to that associated with the donor liver tissue. The type, quantity, and spatial organization of the cells is similar to that found in the donor liver. And because the HCV is replicated in the persisting human hepatocytes, the mouse becomes viremic.

What is claimed is:

1. A method of supporting the replication of hepatitis C virus in an animal model, comprising:
    transplanting viable, hepatitis C virus-infected, human hepatocytes into liver parenchyma of a scid/scid mouse host; and
    maintaining the scid/scid mouse host in a viable state, whereby viable, morphologically intact human hepatocytes persist and hepatitis C virus is replicated in the persisting human hepatocytes.

2. The method in accordance with claim 1 wherein the scid/scid mouse host is an H-$2^d$ scid/scid mouse host.

3. The method in accordance with claim 2 further comprising obtaining the hepatocytes to be transplanted by a percutaneous liver biopsy.

4. The method in accordance with claim 3 further comprising depleting the hepatocytes of leukocytes prior to transplanting.

5. The method in accordance with claim 3 wherein the mouse host is maintained in the viable state for at least about five days.

6. A method of preparing an animal model, which supports the replication of hepatitis C virus comprising:

transplanting viable, hepatitis C virus-infected liver tissue from a human donor into liver parenchyma of a scid/scid mouse host; and maintaining the mouse host, whereby the human liver tissue becomes at least partially vascularized, viable, morphologically intact human hepatocytes persist in the transplanted human liver tissue, and replication of hepatitis C virus is supported in said human hepatocytes.

7. The method in accordance with claim 6 wherein the scid/scid mouse host is an $H-2^d$ scid/scid mouse host.

8. The method in accordance with claim 7 further comprising obtaining the liver tissue to be transplanted by a percutaneous liver biopsy.

9. The method in accordance with claim 8 further comprising depleting the liver tissue of leukocytes prior to transplanting.

10. The method in accordance with claim 8 wherein the mouse host is maintained in the viable state for at least about five days.

11. A scid/scid mouse host wherein the liver comprises viable, hepatitis C virus-infected human liver tissue comprising morphologically intact hepatocytes wherein said liver tissue was transplanted into liver parenchyma of said scid/scid mouse host.

12. A method of preparing a scid/scid mouse comprising hepatitis C virus-infected, human hepatocytes, comprising:

transplanting viable, hepatitis C virus-infected, human hepatocytes into liver parenchyma of said scid/scid mouse host; and maintaining the scid/scid mouse host in a viable state, whereby viable morphologically intact human hepatocytes persist and hepatitis C virus is replicated in the persisting human hepatocytes.

13. The method of claim 12, wherein the scid/scid mouse host is an $H-2^d$ scid/scid mouse host.

14. The method of claim 13, further comprising obtaining the hepatocytes to be transplanted by a percutaneous liver biopsy of a human.

15. The method of claim 14, further comprising depleting the hepatocytes of leukocytes prior to transplanting.

16. The method of claim 14, wherein the mouse host is maintained in the viable state for at least about five days.

17. A method of maintaining hepatitis C virus-infected, human hepatocytes in a mouse, comprising:

transplanting viable, hepatitis C virus-infected, human hepatocytes into liver parenchyma of a scid/scid mouse host; and maintaining the scid/scid mouse host in a viable state, whereby viable, morphologically intact human hepatocytes persist and hepatitis C virus is replicated in the persisting human hepatocytes.

18. The method of claim 17, wherein the scid/scid mouse host is an $H-2^d$ scid/scid mouse host.

19. The method of claim 18, further comprising obtaining the hepatocytes to be transplanted by a percutaneous liver biopsy of a human.

20. The method of claim 18, further comprising depleting the hepatocytes of leukocytes prior to transplanting.

21. The method of claim 18, wherein the mouse host is maintained in the viable state for at least about five days.

22. A method of preparing a scid/scid mouse host comprising hepatitis C virus-infected, human hepatocytes, comprising:

transplanting viable, hepatitis C virus-infected liver tissue from a human donor into liver parenchyma of said scid/scid mouse host; and maintaining the mouse host, whereby the human liver tissue becomes at least partially vascularized, viable, morphologically intact human hepatocytes persist in the transplanted human liver tissue, and replication of hepatitis C virus is supported in said human hepatocytes.

23. The method of claim 22, wherein the scid/scid mouse host is an $H-2^d$ scid/scid mouse host.

24. The method of claim 23, whether comprising obtaining the liver tissue to be transplanted by a percutaneous liver biopsy.

25. The method of claim 24, further comprising depleting the liver tissue of leukocytes prior to transplanting.

26. The method of claim 24, wherein the mouse host is maintained in the viable state for at least about five days.

27. A method of maintaining hepatitis C virus-infected, human hepatocytes in a mouse, comprising:

transplanting viable, hepatitis C virus-infected liver tissue from a human donor into liver parenchyma of a scid/scid mouse host; and maintaining the mouse host, whereby the human liver tissue becomes at least partially vascularized, viable, morphologically intact human hepatocytes persist in the transplanted human liver tissue, and replication of hepatitis C virus is supported in said human hepatocytes.

28. The method of claim 27, wherein the scid/scid mouse host is an $H-2^d$ scid/scid mouse host.

29. The method of claim 28, further comprising obtaining the liver tissue to be transplanted by a percutaneous liver biopsy.

30. The method of claim 29, further comprising depleting the liver tissue of leukocytes prior to transplanting.

31. The method of claim 29, wherein the mouse host is maintained in the viable state for at least about five days.

maintaining the scid/scid mouse host in a viable state, whereby viable morphologically intact human hepatocytes persist and hepatitis C virus is replicated in the persisting human hepatocytes.

* * * * *